(12) United States Patent
Aizawa et al.

(10) Patent No.: US 6,413,495 B1
(45) Date of Patent: Jul. 2, 2002

(54) X-RAY INTERCEPTING METAL COMPLEXES OF CHLORIN DERIVATIVES

(75) Inventors: Katsuo Aizawa, Tokyo; Shinjiro Sumi, Odawara; Hirotada Takahashi, Odawara; Noriaki Aman, Odawara; Yoshihiko Terayama, Odawara; Shuichi Gomi, Yokohama, all of (JP)

(73) Assignee: Meiji Seika Kaisha, Ltd., Tokyo (JP)

(*) Notice: Subject to any disclaimer, the term of this patent is extended or adjusted under 35 U.S.C. 154(b) by 0 days.

(21) Appl. No.: 09/743,448

(22) PCT Filed: Jul. 12, 1999

(86) PCT No.: PCT/JP99/03752

§ 371 (c)(1),
(2), (4) Date: Jan. 10, 2001

(87) PCT Pub. No.: WO00/02882

PCT Pub. Date: Jan. 20, 2000

(30) Foreign Application Priority Data

Jul. 10, 1998 (JP) .......................................... 10-195717

(51) Int. Cl.⁷ ..................... C07D 487/22; A61K 31/409
(52) U.S. Cl. ....................................... 424/9.42; 540/145
(58) Field of Search ........................... 540/145; 424/9.42

(56) References Cited

U.S. PATENT DOCUMENTS 4,693,885 A * 9/1987 Bommer et al. ................ 424/2

* cited by examiner

*Primary Examiner*—Richard L. Raymond
*Assistant Examiner*—Kahsay Habte
(74) *Attorney, Agent, or Firm*—Larson & Taylor PLC (57) ABSTRACT

An X-ray-intercepting gold complex of mono-L-aspartyl (or mono-L-glutamyl) chlorin e6 or a salt thereof is used in the therapy of the tumor, cancer or arteriosclerosis lesions by X-ray irradiation. The complex provides a sharp x-ray image of tumor, solid cancer or lesions of arteriosclerosis. A similar platinum complex may also be utilized.

16 Claims, 4 Drawing Sheets

X-RAY INTERCEPTING METAL COMPLEXES OF CHLORIN DERIVATIVES

The present application is a National Phase of PCT/JP99/03752 filed Jul. 12, 1999.

TECHNICAL FIELD

This invention relates to a novel, X-ray-intercepting metal complex of a chlorin e6 derivative which is useful for detection, diagnosis and/or therapy of tumor or solid cancer or lesions of arteriosclerosis by X-ray radiography or X-ray irradiation. More specifically, this invention relates to a novel X-ray-intercepting gold complex or platinum complex of mono-L-aspartyl chlorin e6 or mono-L-glutamyl chlorin e6, which is capable of administering to a host mammal for the purposes of conducting detection, diagnosis and/or therapy by X-ray radiography or X-ray irradiation of tumor or solid cancer or lesions of arteriosclerosis (for example, atherosclerosis layer in an inner wall of artery) formed in the host mammal, and which is able to accumulate and distribute preferentially within the tumor, solid cancer or the lesions of arteriosclerosis and can act not only as a contrast medium capable of affording sharp X-ray image of the tumor, solid cancer and lesions of arteriosclerosis, but also is effective in therapeutic treatment of the tumor, solid cancer or the lesions of arteriosclerosis.

This invention also relates to a pharmaceutical composition comprising as an active ingredient the above-mentioned novel X-ray-intercepting gold complex or platinum complex of the chlorin e6 derivative. This invention further includes methods for the detection, diagnosis and/or therapy of tumor, solid cancer or lesions of arteriosclerosis formed in the host mammal, by using the novel X-ray-intercepting gold complex or platinum complex of the chlorin e6 derivative as above-mentioned.

BACKGROUND ART

Photochemotherapy or photodynamic therapy so called is a method for the therapeutic treatment of cancer or tumor and arteriosclerosis or other diseases, which comprises administration of a photosensitive substance capable of being excited by irradiation of ultraviolet ray or laser light. That is, it is the chemotherapy wherein ultraviolet ray or laser light is irradiated to the tissue of cancer or tumor or to lesions of arteriosclerosis in which the photosensitive substance pre-administered has been present and accumulated, or ultraviolet ray or laser light is irradiated to a bloodstream extracorporeally circulated of blood containing the photosensitive substance, so that the photosensitive substance can be excited to effect the therapeutic treatment as intended.

As the photosensitive substances to be used in such photochemotherapy or photodynamic therapy, there are known hematoporphyrin derivatives and chlorin derivatives (refer, for example, to Japanese Patent Application Publication Kokai Hei 2-138280 (patented under Japanese Patent No. 2520735), the corresponding European Patent Application Publication No. 350948 A1 and Japanese Patent Publications Hei 6-88902 and Hei 6-89000, as well as U.S. Pat. Nos. 4,656,186, 4,675,338, 4,693,885 and 4,997,639 specifications). Further, one article reports a result of clinical study on photochemotherapy applied to superficial early stage cancers where a hematoporphyrin derivative is administered (refer to the Journal of the Society of Cancer Therapy of Japan, Vol. 29, pp. 1757–1766 (1994)). In particular, Japanese Patent Publications Hei 6-88902 and Hei 6-89000 and U.S. Pat. Nos. 4,656,186, 4,675,338 and 4,693,885 specifications mentioned above disclose the use, as a photochemotherapeutic agent in the diagnosis and therapeutic treatment of tumor or solid cancer, of an appropriate chlorin derivative, particularly of mono-L-aspartyl chlorin e6 and mono-L-glutamyl chlorin e6, which is represented by the following general formula (A)

(A)

wherein n stands for an integer of 1 or 2, or a salt thereof. The literatures further disclose that mono-L-aspartyl chlorin e6 or mono-L-glutamyl chlorin e6 or a salt thereof is preferentially up-taken within the tissue of tumor or solid cancer and is accumulated therein.

U.S. Pat. No. 4,997,639 specification discloses that mono-L-aspartyl chlorin e6 or other suitable chlorin derivative or a salt thereof, if administered to a host mammal, can preferentially be up-taken in such a part or parts of the host body where cholesterol has deposited therein and has been accumulated, and thus it is effective to detect the cholesterol-accumulated part by such photodynamic diagnosis method. Further, Japanese Patent Application Publication Kokai Hei 4-330013 and U.S. Pat. No. 5,308,861 specification disclose that mono-L-aspartyl chlorin e6 or other suitable chlorin derivative or a salt thereof may preferentially be accumulated in the lesions of arteriosclerosis as formed in the inner wall of artery which are accompanying with coronary arteriosclerosis inductive of cardiac infarct or angina pectoris; arteriosclerosis obliterans as induced in limb peripheral artery or aorta abdominalis; and cerebral arteriosclerosis inductive of transient cerebral ischemia or cerebral infarct, and that they may be useful for diagnosis of such lesions of arteriosclerosis by a photodynamic diagnosis method, and also that the irradiation of laser light to such lesions containing the chlorin derivative so accumulated can bring about some remedying and curing effects on the lesions of arteriosclerosis. Japanese Patent Application Publication Kokai Hei 4-330013 and U.S. Pat. No. 5,308,861 specification further report that the chlorin derivative is superior to the hematoporphyrin derivative in respect of the accumulating ability and in respect of the curative effect on the lesions of arteriosclerosis, as viewed from the results of tests of the chlorin derivative in comparison with the hematoporphyrin derivative.

Furthermore, Japanese Patent Publications Hei 6-88902 and Hei 6-89000 and U.S. Pat. Nos. 4,675,338 and 4,693,885 mentioned above disclose that the chlorin derivative described therein can form a metal complex with magnesium, iron, zinc, nickel, cobalt or copper. Further, Japanese Patent specification No. 2520735 (issued on Jul.

31, 1996) and European Patent Application Publication No. 350948A mentioned above disclose that metal porphyrins containing zinc, iron, copper, manganese, potassium, indium or other metals as the coordinating metal are useful in the photodynamic diagnosis or photodynamic therapy of cancers or tumors.

Further, a Japanese journal, YAKUGAKU ZASSHI Vol. 84, No. 12, pp. 1152–1157 (1964) reports that chlorophyllin as derived from chlorophyll can form a metal chelate compound with magnesium, cobalt, manganese, vanadium, silver or gold.

As far as the inventors of this invention have been aware of, however, there is known no metal complex of mono-L-aspartyl chlorin e6 or mono-L-glutamyl chlorin e6 with gold or platinum, up to date.

On the other hand, in the photochemotherapy and photodynamic diagnosis with using the hematoporphyrin derivatives or chlorin derivatives as a photosensitive substance, there has been used, in most cases, ultraviolet ray or laser light of a wavelength in a range of 300–800 nm as the radiation for exciting said photosensitive substance to emit the fluorescence therefrom.

However, the depth to which a laser light is capable of transmitting in the internal tissues of the host body is 5 mm–8 mm under the operating conditions used in the usual photochemotherapy and is 10 mm–20 mm at most even in such cases where a peak output of the laser light is elevated much (refer to Biotherapy, Vol. 7, pp. 673–680 (1993)). In such photochemotherapy as targetted on tissues of cancer or tumors which are existing in deep parts of the host body, it is necessary to conduct a surgical invasion with a danger or risk for patients, for example, a surgical operation for incision to reach the cancer or tumor, pouring of a photosensitive substance into the region of such cancer or tumor tissue or surgical insertion of a laser irradiation device into the body, and the like. In such cases where the photochemotherapy is directed to treatment of the arteriosclerosis, it becomes necessary to perform a special and troublesome surgical invasion, such as an insertion of a laser irradiation device into the blood vessels. Since, however, such a surgical invasion into a tissue or organ existing in the internal deep part of the host body is a complicated operation and can always-involve a danger or risk unexpectable, it is an operation to be avoided, if possible, as a means for the medical treatment.

We, the inventors of this invention, have now made extensive investigations with our intention of developing a novel photochemotherapeutical method and a novel photodynamic diagnosis method which can operate without the necessity of performing any surgical invasion in a dangerous and complicated way, even in such cases when tumor or solid cancer or lesions of arteriosclerosis to be diagnosed or treated is present in the deep region of the patient body to which the laser light used in the prior art photochemotherapeutic treatments cannot reach.

Upon investigating this problem, we have paid attention to the fact that a known compound, mono-L-aspartyl chlorin e6 or mono-L-gultamyl chlorin e6 or a water-soluble alkali metal salt thereof, when it has been administered to the patient, exhibits such characteristic property that it can accumulate preferentially within the tumor or solid cancer tissue or the lesions of arteriosclerosis present in the patient's body and it can also be excreted rapidly from the body after a certain period of time. We also have gave attention to the fact that x-ray has a special property that it can reach whatever depth within the patient body and can also pass through the body if the wavelength and intensity of X-ray are appropriately chosen, in contrast to the ultraviolet rays and laser lights which have been used as the exciting radiation for the photosensitive substance-in the prior art photochemotherapy.

On the basis of these attentions and conceptions, we have now carried out extensive investigations to creat such novel chlorin e6 derivatives which are derived from mono-L-aspartyl chlorin e6 or mono-L-glutamyl chlorin e6, and which have been imparted with such additional properties that the novel chlorin e6 derivatives prepared are capable of intercepting the X-ray and also are capable of being excited with the irradiation of X-ray thereto.

As a result of our various investigations, we have now succeeded in synthesizing and obtaining such a novel, X-ray-intercepting gold complex of mono-L-aspartyl chlorin e6 or mono-L-glutamyl chlorin e6 or a salt thereof, which is produced by combinating through a coordinate linkage or chelation bond, with the chlorin ring of the mono-L-aspartyl chlorin e6 or mono-L-glutamyl chlorin e6 molecule, a less toxic gold atom that exhibits an excellent X-ray-intercepting ability against X-ray having a range of wavelengths easily passing through the vital animal body.

We have now further found that, when the novel X-ray-intercepting gold complex of mono-L-aspartyl chlorin e6 or mono-L-glutamyl chlorin e6 or a sodium salt thereof thus obtained is administered either to a host having a solid ascites carcinoma in the abdominal region, or to a host having the lesions of arteriosclerosis, the said X-ray-intercepting gold complex can accumulate preferentially within the tumor tissue or the lesions of arteriosclerosis in 1–3 hours after the administration of said gold complex, and that when the said X-ray-intercepting gold complex so accumulated is irradiated with an X-ray beam containing therein X-ray of wavelength of 0.153 Å by a technique of computed X-ray tomography, it can give a sharp X-ray image of the tumor tissue or lesions of arteriosclerosis, and that if the irradiation time of said X-ray beam is adjusted, the said X-ray-intercepting gold complex so accumulated is excited and can exert a cytocidal action against the ascites carcinoma cells or a destroying action against the cholesterol having accumulated in the lesions of arteriosclerosis. We have further found that generally, the above-mentioned novel gold complex of mono-L-aspartyl (or mono-L-glutamyl)chlorin e6 or their salts, when administered, can accumulate preferentially within the tumor, solid cancer or lesions of arteriosclerosis as developed in a mammal host (including human and domestic animals such as horse, cattle and sheep, and companion animals such as dogs and cats) and can function to give a sharp X-ray image thereof upon being irradiated with X-ray beam containing therein an X-ray of wavelength of 0.153 Å by the X-ray radiography, and it further can act as an agent for curing the tumor or solid cancer and also as an agent for curing the lesions of arteriosclerosis. This invention has been completed on the basis of these findings as above.

According to a first aspect of this invention for a broadest concept, therefore, there is provided as a novel compound, an X-ray-intercepting gold complex of mono-L-aspartyl chlorin e6 or mono-L-glutamyl chlorin e6, which is produced by coordinate bond or chelation of a gold cation with the chlorin ring of mono-L-aspartyl chlorin e6 or mono-L-glutamyl chlorin e6, or a pharmacologically acceptable salt thereof.

The X-ray-intercepting gold complex according to the first aspect of this invention can, in general, be expressed as an X-ray-intercepting gold complex of mono-L-aspartyl chlorin e6 or mono-L-glutamyl chlorin e6 with a mono, di or trivalent gold atom, which is represented by the following general formula (I)

(I)

wherein Au stands for a gold atom, m stands for an integer of 1, 2 or 3 and n stands for an integer of 1 or 2. The gold atom present in the gold complex as represented by the general formula (I) may be a cation of mono, di or trivalent.

Among the gold complexes which can be represented by the general formula (I) above, such the gold complex where n=1 is a gold complex of mono-L-aspartyl chlorin e6 in which L-aspartic acid was bonded through an amido-linkage to the side chain —$CH_2COOH$ at the 20-position of the chlorin ring shown in the formula (I) above. Among the gold complexes which can be represented by the general formula (I) above, such gold complex where n=2 is the gold complex of mono-L-glutamyl chlorin e6 in which L-glutamic acid, instead of L-aspartic acid, was bonded through an amido-linkage.

The gold complex of the chlorin e6 derivative having the general formula (I) according to this invention may form a salt with a base at the free carboxyl group thereof. As the salts formed by the reaction with bases, there are exemplified sodium, potassium, calcium, magnesium or ammonium salts and also triethylammonium, trimethylammonium, morpholine and piperidine salts. Further, the gold complex of the chlorin e6 derivative having the general formula (I) may form a salt by bonding their basic group with an inorganic acid or an organic acid. As the salt formed by the reaction with an acid, there are exemplified hydrochloride, sulfate, nitrate, phosphate, acetate, formate, and the like.

In a preferred embodiment of the first aspect of this invention, the gold complex of the chlorin e6 derivative having the general formula (I) above is an X-ray-intercepting gold complex of mono-L-aspartyl chlorin e6 or mono-L-glutamyl chlorin e6 with a trivalent gold atom, which is represented by the following general formula (Ia)

(Ia)

wherein Au stands for a gold atom and n stands for an integer of 1 or 2.

A particularly preferred example of the gold complex of the general formula (Ia) is the X-ray-intercepting gold complex of mono-L-aspartyl chlorin e6 with a trivalent gold atom, which is represented by the following formula (Ia-1)

(Ia-1)

The mono-L-aspartyl chlorin e6-gold complex represented by the formula (Ia-1) was obtained in Example 1 given hereinafter in the form of a dark green colored amorphous powdery substance which shows no definite melting point, but decomposes at or near 270° C. and which is represented by molecular formula (empirical formula): $C_{38}H_{38}AuN_5O_9$, by a process comprising reacting mono-L-aspartyl chlorin e6 tetrasodium salt with 1~2 molar equivalents of hydrogen tetrachloroaurate ($HAuCl_4$) in a 1/15M phosphate buffer solution (pH 7.5), followed by purifying the resultant reaction product in a suitable manner. There was also obtained a trisodium salt of mono-L-aspartyl chlorin e6-gold complex of the formula (Ia-1).

Mono-L-aspartyl chlorin e6 and mono-L-glutamyl chlorin e6, which may be used as the starting materials for the preparation of the gold complex of the chlorin e6 derivative having the general formula (I) according to a preferred embodiment of the first aspect of this invention, are such compounds as obtained by the process for the preparation thereof as described, for example, in Example 19 and Example 21, respectively, of Japanese Patent Publication Hei 6-88902 or U.S. Pat. No. 4,675,338.

In order to produce the gold complex of the chlorin e6 derivative having the general formula (I) according to a preferred embodiment of the first aspect of this invention, there can generally be practiced a process which comprises dissolving mono-L-aspartyl chlorin e6 or mono-L-glutamyl chlorin e6 or tetrasodium salt thereof and a chloride or fluoride of a mono, di or trivalent gold atom, preferably hydrogen tetrachloroaurate ($HAuCl_4$) used in an appropriate molar equivalent into a suitable solvent, preferably a phosphate buffer solution of pH 7.0~8.0, and reacting both the reactants at a temperature of 0~50° C., acidifying the resulting reaction solution with hydrochloric acid after the completion of the reaction, thereby precipitating the gold complex product from the reaction solution, and purifying the so precipitated gold complex product by using a reversed phase column.

In order to produce the mono-L-aspartyl chlorin e6 gold complex of the formula (Ia-1) above and isolate it as a pure product, it is convenient to use such a process which comprises the following steps of reacting mono-L-aspartyl chlorin e6 tetrasodium salt with 1~2 molar equivalents of hydrogen tetrachloroaurate ($HAuCl_4$) in a phosphate buffer solution having a $\frac{1}{10}$~$\frac{1}{20}$ molar concentration at a temperature of 0~50° C. until the reaction is completed, then adjusting the pH of the resulting reaction solution with addition of a dilute hydrochloric acid to pH 2.5~3.5, thereby depositing a precipitate comprising the gold complex of mono-L-aspartyl chlorin e6, collecting the precipitate, then dissolving the precipitate so collected in a phosphate buffer solution of $\frac{1}{10}$~$\frac{1}{20}$ molar concentration (pH 7.0~8.0) in order to effect a purification of the gold complex, passing the resulting solution through a reversed phase column where a gel of octadecylsilica (ODS)is used as the immobile phase and water containing 5 5~15% (volume %) of methanol is used as the mobile phase, then collecting in fractions the effluent from the reversed phase column, concentrating the effluent fractions containing singly the mono-L-aspartyl chlorin e6-gold complex under a reduced pressure, adjusting the pH of the resultant concentrated solution with a dilute hydrochloric acid to pH 2.5~3.5, thereby depositing a precipitate of dark green color, collecting the precipitate, washing the resulting precipitate with water containing 40~50% (volume %) of acetone, separating the precipitate from the aqueous acetone by centrifugation, and drying further the precipitate made of said gold complex under a reduced pressure.

The acute toxicity, as tested by oral administration to CD-1 mice (male), of mono-L-aspartyl chlorin e6 tetrasodium salt is already known to be such that its 50% lethal dose is 164 mg/kg, and thus the compound is of a low toxicity (refer to Japanese Patent Application Publication Kokai Hei 9-71531). The acute toxicity of a sodium salt of the mono-L-aspartyl chlorin e6-gold complex having the above-mentioned formula (Ia-1) upon its oral administration is found to be substantially same as that of the mono-L-aspartyl chlorin e6 tetrasodium salt, and thus there is observed no increase in the toxicity by the complexing of the latter salt compound with a gold atom.

Gold atom can possess the X-ray-intercepting ability and also has such a special property that the gold atom absorbs an X-ray of a specific wavelength (0.153 Å) to convert into an excited state, and that when the gold atom transits into the ground or normal state back from the excited state, it does not involve the emission of photon but, instead thereof, can involve emission of electron (namely, Auger effect) owing to that an energy can be given to other electron within the atom of gold.

The gold atom present in the chlorin e6 derivative-gold complex of this invention also has same properties as above, so that the gold complex of this invention has an X-ray-intercepting ability and is therefore capable of giving an X-ray image by X-ray radiography. Further, the gold complex of this invention in able to absorb an X-ray of 0.153 Å wavelength and convert into the excited state and then emit the electron upon the transition to go back into the ground state, so that, due to the action of the emitted electron, the gold complex of this invention can impair the cells of the tumor or cancer in which the gold complex has specifically accumulated, or the gold complex of this invention can promote decomposition of the cholesterol present in the lesions of arteriosclerosis upon the irradiation with X-ray.

Thus, in accordance with this invention, the gold complex of this invention is imparted not only with the ability to accumulate preferentially in the tumor or cancer tissue or in the arteriosclerotic lesions as exhibited characteristically by the mono-L-aspartyl chlorin e6 or mono-L-glutamyl chlorin e6, but also is imparted by the complexing gold atom with the X-ray-intercepting ability as well as the activity of emitting electron under irradiation of X-ray, whereby the gold complex of this invention can have gained the capability of making the diagnosis by X-ray radiography, as well as the function of imparing the cells of tumor or cancer and the function of destroying the arteriosclerotic lesions under irradiation of X-ray.

According to a second aspect of this invention, there is provided a pharmaceutical composition, comprising as an active ingredient, an X-ray-intercepting gold complex of mono-L-aspartyl chlorin e6 or mono-L-glutamyl chlorin e6, which is produced by coordinate bond or chelation of the chlorin ring of mono-L-aspartyl chlorin e6 or mono-L-glutamyl chlorin e6 with a gold cation, or a pharmacologically acceptable salt thereof, in combination with a pharmaceutically acceptable solid or liquid carrier.

The above-mentioned X-ray-intercepting gold complex which is contained as the active ingredient in the pharmaceutical composition according to the second aspect of this invention, may, in general, be an X-ray-intercepting gold complex of mono-L-aspartyl chlorin e6 or mono-L-glutamyl chlorin e6 with a mono, di or trivalent gold atom, which is represented by the following formula (I)

(I)

wherein Au stands for a gold atom, m stands for an integer of 1, 2 or 3 and n stands for an integer of 1 or 2. Said gold complex may preferably be an X-ray-intercepting gold complex of mono-L-aspartyl chlorin e6 or mono-L-glutamyl chlorin e6 with a trivalent gold atom, which is represented by the following formula (Ia)

(Ia)

wherein Au stands for a gold atom and n stands for an integer of 1 or 2.

The pharmaceutical composition according to the second aspect of this invention may be administered for the purposes of detection and diagnosis of the tissue of tumor or solid cancer as formed in the mammal host by X-ray radiography, and it may also be administered for the purpose of detection of the tissue of tumor or solid cancer as formed in the mammal host by X-ray radiography, and further for the purpose of therapeutic treatment or remedy of the so detected tumor or solid cancer by subsequent irradiation of X-ray.

The pharmaceutical composition according to the second aspect of this invention may also be administered for the purposes of detection and diagnosis of the lesions of arteriosclerosis or the cholesterol-accumulated regions of artery in the mammal host by X-ray radiography, and it may also be administered for the purpose of detection of the lesions of arteriosclerosis or the cholesterol-accumulated regions of artery in the mammal host, by X-ray radiography and further for the purpose of treatment or remedy of the detected lesions of arteriosclerosis or the detected cholesterol-accumulated regions of artery by subsequent irradiation of X-ray.

Concretely, the pharmaceutical composition according to the second aspect of this invention is effective to conduct detection, diagnosis and therapy of such tumor existing at a deep position within the host body, for example, cerebral tumor, lung cancer, gastric cancer, liver cancer, pancreatic cancer, uterine cancer, prostatic cancer, kidney cancer, esophagial cancer, etc., and also is effective to conduct detection, diagnosis and therapy of such tumor or cancer as developed on or near the body surface. The composition of this invention is also effective to conduct detection, diagnosis and therapy of the lesions of arteriosclerosis, for example, coronary arteriosclerosis which may induce cardiac infarct or agina pectoris; arteriosclerosis obliterans which may occur in limb peripheral artery or aorta abdominalis; and cerebral arteriosclerosis which may induce transient cerebral ischemia, and so on.

The gold complex, which is incorporated as the active ingredient in the composition according to the second aspect of this invention, may be administered orally or by intravenous or intramuscular injections or by other parenteral routes. The compound usable as the active ingredient may also be administered percutaneously. The compound usable as the active ingredient may also be administered locally, for example, by injecting it locally and directly into the tumor tissue existing at a deep position of the host body, or by administering it locally near the lesions of arteriosclerosis by means of a special catheter. The composition according to the second aspect of this invention may contain the active ingredient compound in the form of a sodium salt thereof and may further be formulated in a lyophilized sterile preparation containing no pyrogen.

In cases where the pharmaceutical composition according to the second aspect of this invention is to be orally administered, the active ingredient compound-may be mixed with a solid or liquid carrier and may be formulated in the form of tablets, buccal tablets, troches, capsules, suspensions, syrups and the like.

In cases where the pharmaceutical composition according to the second aspect of this invention is in the form of an injection preparation, the active ingredient compound may be formulated in the form of a sterile aqueous solution or dispersion or a sterile lyophilized preparation containing the active compound. As liquid carriers, there are exemplified preferably water, saline, ethanol, aqueous ethanol, glycerol, propylene glycol and vegetable oils. In most cases, it is also preferred to incorporate therein an isotonic agent, for example, sugar or sodium chloride.

The dose of administration of the gold complex of chlorin e6 derivative according to this invention may vary depending upon the subject and purposes of the detection, diagnosis or therapy of the lesions to be targeted or treated, and the gold complex may, in general, be administered in adult at a single dose of 0.01~50 mg/kg, preferably of 0.1~10 mg/kg of the body weight.

According to a third aspect of this invention, there is provided use of an X-ray-intercepting gold complex of the chlorin e6 derivative having the above-mentioned general formula (I) or a salt thereof, or an X-ray-intercepting gold complex of the chlorin e6 derivative having the general formula (Ia) or a salt thereof, in the manufacture of the pharmaceutical composition to be used for conducting the detection, diagnosis and/or therapy of the tissue of tumor or solid cancer by means of X-ray irradiation.

According to a fourth aspect of this invention, there is provided use of an X-ray-intercepting gold complex of the chlorin e6 derivative having the above-mentioned general formula (I) or a salt thereof, or an X-ray-intercepting gold complex of the chlorin e6 derivative having the general formula (Ia) or a salt thereof, in the manufacture of the pharmaceutical composition to be used for conducting detection, diagnosis and/or therapy of the lesions of arteriosclerosis or the cholesterol-accumulated regions of artery by means of X-ray irradiation.

Further, according to a fifth aspect of this invention, there is provided a method for the detection and diagnosis of tissue of tumor or solid cancer, which comprises administering to a mammal host having a tumor or solid cancer an X-ray-intercepting gold complex of the chlorin e6 derivative having the general formula (I) or a salt thereof, or an X-ray-intercepting gold complex of the chlorin e6 derivative having the general formula (Ia) or a salt thereof according to the first aspect of this invention, particularly the mono-L-aspartyl chlorin e6-gold complex of the formula (Ia-1) or a sodium salt thereof, in an amount of the gold complex effective to permit the gold complex to accumulate in the tumor or solid cancer tissue, then irradiating from outside of the host body an X-ray beam containing X-ray of a wavelength of 0.153 Å towards the tumor or cancer, and taking a photograph of X-ray image of the tumor or solid cancer tissue having contained therein said gold complex, on an X-ray film by a technique of computed X-ray tomography, and making diagnosis of the tumor or cancer tissue.

Furthermore, according to a sixth aspect of this invention, there is provided a method for the detection and therapy of a tumor or solid cancer, which comprises administering to a mammal host having a tumor or solid cancer an X-ray-intercepting gold complex of the chlorin e6 derivative having the general formula (I) or a salt thereof, or an X-ray-intercepting gold complex of the chlorin e6 derivative having the general formula (Ia) or a salt thereof according to the first aspect of this invention, particularly the mono-L-aspartyl chlorin e6-gold complex of the formula (Ia-1) or a sodium salt thereof, in an amount of the gold complex effective to permit the gold complex to accumulate in the tumor or solid cancer tissue, then irradiating from outside of the host body an X-ray beam containing X-ray of a wavelength of 0.153 Å towards the tumor or cancer, and taking a photograph or of X-ray image of the tumor or solid cancer tissue having contained therein said gold complex, on an X-ray film by a technique of computed X-ray tomography, to detect the region of the tumor or solid cancer, and thereafter further irradiating to the region of the tumor or solid cancer an X-ray beam containing X-ray of a wavelength of 0.153 Å, whereby at least a portion of the cells of the tumor or solid cancer is killed by the action of the gold complex as excited with the so irradiated X-ray and also by the electron as emitted from the gold atom of said complex.

The method of the fifth aspect of this invention, as well as the method of the sixth aspect of this invention are applicable to cerebral tumor, lung cancer, gastric cancer, liver cancer, pancreatic cancer, uterine cancer, prostatic cancer, kidney cancer, esophagial cancer of a mammal host as the target to be treated.

Further, according to a seventh aspect of this invention, there is provided a method for the detection and therapy of lesions of arteriosclerosis, which comprises administering to a mammal host having an arteriosclerosis a gold complex of the chlorin e6 derivative having the general formula (I) above or a salt thereof, or a gold complex of the chlorin e6 derivative having the general formula (Ia) above or a salt thereof, particularly the mono-L-aspartyl chlorin e6-gold complex of the formula (Ia-1) or a sodium salt thereof, in an amount of the gold complex effective to permit the gold complex to accumulate in the lesions of arteriosclerosis, then irradiating from outside of the host body an X-ray beam containing X-ray of a wavelength of 0.153 Å towards the arteriosclerosis lesions, and taking a photograph of X-ray image of the lesions of arteriosclerosis having contained therein said gold complex, on an X-ray film by a technique of computed X-ray tomography, to detect the region of the lesions of arteriosclerosis, and thereafter further irradiating to the region of the lesions of arteriosclerosis an X-ray beam containing X-ray of a wavelength of 0.153 Å, whereby the cholesterol-accumulated parts present within the said lesions of arteriosclerosis are destroyed by the actions of the gold complex as excited with the so irradiated X-ray and also by the electron as emitted from the gold atom of said complex.

The method according to the seventh aspect of this invention is applicable to lesions of coronary arteriosclerosis which may induce cardiac infarct or agina pectoris; arteriosclerosis obliterans which may occur in limb peripheral artery or aorta abdominalis; cerebral arteriosclerosis which may induce transient cerebral ischemia, as the targets to be treated. The X-ray beam containing the X-ray of wavelength of 0.153 Å may be obtained by utilizing a known X-ray generating apparatus.

We have prosecuted our investigations further. As a result of these further investigations, we have now found that, like the gold, platinum can also form an X-ray-intercepting platinum complex of mono-L-aspartyl chlorin e6 or mono-L-glutamyl chlorin e6 by coordinate bond or chelation of the platinum atom with the chlorin ring of said chlorin e6 derivative.

According to an eighth aspect of this invention, therefore, there is provided as the novel compound an X-ray-intercepting platinum complex of mono-L-aspartyl chlorin e6 or mono-L-glutamyl chlorin e6, which is produced by coordinate bond or chelation of a platinum cation with the chlorin ring of mono-L-aspartyl chlorin e6 mono-L-glutamyl chlorin e6, or a pharmacologically acceptable salt thereof.

The X-ray-intercepting platinum complex according to the eighth aspect of this invention may, in general, be expressed to be an X-ray-intercepting platinum complex of mono-L-aspartyl chlorin e6 or mono-L-glutamyl chlorin e6 with a di or trivalent platinum atom, which is represented by the following general formula (II)

(II)

wherein Pt stands for a platinum atom, z stands for an integer of 1 or 2 and n stands for an integer of 1 or 2.

In a preferred embodiment of the eighth aspect of this invention, the platinum complex of the chlorin e6 derivative which is represented by the general formula (II) above may be an X-ray-intercepting platinum complex of mono-L-aspartyl chlorin e6 or mono-L-glutamyl chlorin e6 with a tetravalent platinum atom, which is represented by the following general formula (IIa)

(IIa)

wherein n stands for an integer of 1 or 2.

The platinum complex of mono-L-aspartyl chlorin e6 or mono-L-glutamyl chlorin e6 as represented by the general formula (IIa) above may form a disodium salt.

Platinum atom can possess the X-ray-intercepting ability and also has such a special property that the platinum atom absorbs an X-ray of a specific wavelength (0.158 Å) to convert into an excited state, and that when the platinum atom transits into the ground state from the excited state, it does not involve the emission of photon but, instead thereof, can involve emission of electron (namely, Auger effect) owing to that an energy can be given to other electron within the atom of platinum.

The platinum atom present in the platinum complex of the chlorin derivative according to this invention also has same properties as above, and hence the platinum complex of this invention has the X-ray-intercepting ability and thus is capable of giving the X-ray image by X-ray radiography. Further, the platinum complex of this invention is able to absorb the X-ray of 0.158 Å wavelength and convert into the excited state.

When the platinum complex as excited transits back into the ground state, it emits the electron, so that, due to the action of the so emitted electron, the platinum complex of this invention can impair the cells of the tumor or cancer in which the platinum complex has specifically accumulated, or the platinum complex of this invention can promote decomposition of the cholesterol present in the lesions of arteriosclerosis upon the irradiation with the X-ray.

Therefore, the X-ray-intercepting platinum complex of the chlorin e6 derivative or a salt thereof according to the eighth aspect of this invention, similarly to the X-ray-intercepting gold complex of the chlorin e6 derivative or a salt thereof according to the first aspect of this invention, are utilizable for conducting the detection, diagnosis and therapy of the tumor or solid cancer or the lesions of arteriosclerosis.

The platinum complex of the chlorin e6 derivative having the of general formula (II) may be prepared by reacting mono-L-aspartyl (or mono-L-glutamyl) chlorin e6 tetrasodium salt with a chloride or fluoride of a di or tetravalent platinum atom, preferably hydrogen tetrachloroplatinate or hydrogen hexachloroplatinate, in an amount of 2~5 molar equivalents in a phosphate buffer solution at a temperature of 0~50° C.

BEST MODE FOR CARRYING OUT THE INVENTION

Now, this invention is concretely illustrated with reference to the following Examples and Test Examples, but this invention is not limited thereto.

EXAMPLE 1

Preparation of the Mono-L-aspartyl Chlorin e6-gold Complex

Five grams of mono-L-aspartyl chlorin e6 tetra-sodium salt, which was synthesized in accordance with the process described in Example of Japanese Patent Publication Hei 6-88902 (or U.S. Pat. No. 4,675,338) and which gives the infrared absorption spectrum shown in FIG. 1 of the attached Drawings, were dissolved in 900 ml of a 1/15M phosphate buffer solution (pH 7.5). To the resulting solution was added an aqueous solution of hydrogen tetrachloroaurate tetrahydrate ($HAuCl_4 \cdot 4H_2O$) (3 g) in water (100 ml). The amount of hydrogen tetrachloroaurate tetrahydrate added was about 1.1 molar equivalents to 1 mole of mono-L-aspartyl chlorin e6 tetrasodium salt.

The reaction mixture was stirred at room temperature. Samples of the reaction solution were taken out at certain intervals of time and were analyzed by a silica gel thin-layer chromatography (TLC) as undermentioned, in order to examine the presence of the spot of mono-L-aspartyl chlorin e6 (Rf value: 0.71). The reaction was stopped at the point of time when the reaction solution showed no spot of the mono-L-aspartyl chlorin e6 on this TLC. The reaction solution of dark green color as obtained after the completed reaction was adjusted to pH 2.5~3.5 with addition of 3N hydrochloric acid, resulting in deposition of a dark green precipitate. The precipitate comprising the mono-L-aspartyl chlorin e6-gold complex was collected by centrifugation.

For the purpose of effecting the purification, the above-mentioned precipitate was dissolved in a small volume of a 1/15M phosphate buffer solution (pH 7.5). The resulting solution was passed into a reversed phase column with using as the immobile phase octadecylsilica (ODS) gel [500 g, Cosmosil 75$C_{18}$ (a product of Nakaraitesk Co.) and with using as the mobile phase water containing 10% methanol. The effluent from the column was collected in 2 ml-fractions. Fractions which were found to contain singly the mono-L-aspartyl chlorin e6-gold complex were combined and concentrated under a reduced pressure to remove methanol. The concentrated solution so obtained was adjusted to pH 2.5~3.5 with addition of 3N hydrochloric acid, thereby to deposit a dark green colored precipitate. The precipitate so deposited was filtered and washed with 50% aqueous acetone. The precipitate thus washed was then separated from the aqueous acetone by centrifugation. The dark green colored solid so obtained was dried under a reduced pressure to afford the mono-L-aspartyl chlorin e6-gold complex as an amorphous powder of dark green color (yield: about 450 mg). This powdery substance with dark green color did not show any definite melting point but decomposed at 270° C.

The mono-L-aspartyl chlorin e6-gold complex so obtained as the dark green colored amorphous powder in the above was subjected to a thin layer chromatography (TLC) with using as the thin layer plate Baker Si—$C_{18}$ (a product of J. T. Baker Co.) and using as the developing solvent methanol-1/15M phosphate buffer solution (=4:1)(pH 7.0), when the gold complex so chromatographed gave an Rf value of 0.77.

Figure 3:
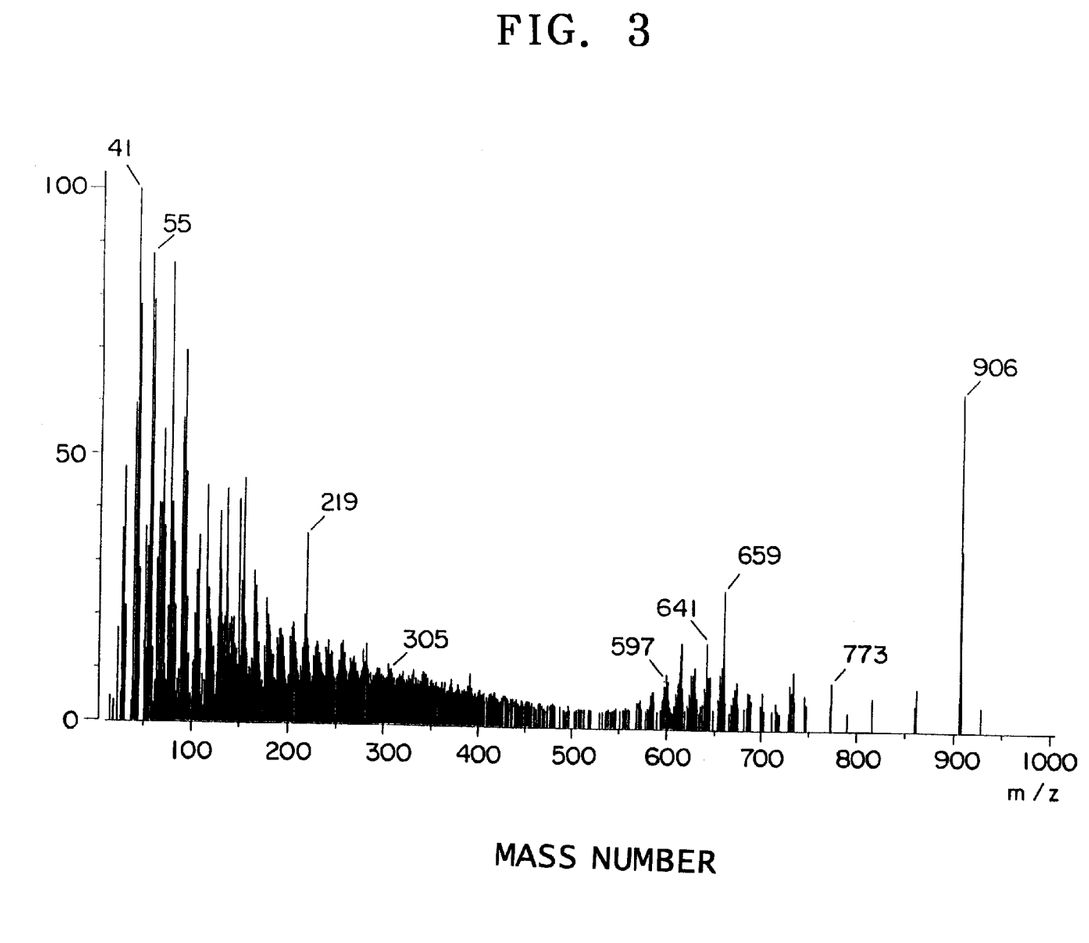
FIG. 3 shows a mass spectrum of mono-L-aspartyl chlorin e6-gold complex as prepared in Example 1 hereinafter given.

Further, the gold complex as obtained was examined for ultraviolet absorption spectrum, infrared absorption spectrum, mass spectrum, $^1$H-NMR spectrum, elementary analysis and atomic absorption spectrum. The mass spectrum as measured is shown in FIG. 3 of the attached Drawings. The results of various measurements are shown below.

UV λmax: 621 nm (O.D.=0.109), 384 nm (O.D.=0.331), (where the concentration at the measurement is 4 μg/ml.); Mass m/z: 906; Elementary analysis; Calculated (as $C_{38}H_{38}AuN_5O_9$): C, 50.4% H, 4.2%, N, 7.7%, Ash, 21.8%; Found: C, 49.6%, H, 4.6%, N, 7.5%, Ash, 20.7%; Atomic absorption of gold: Calculated (as $C_{38}H_{38}AuN_5O_9$): 21.8%; Found: 17.4%.

$^1$H-NMR: Mono-L-aspartyl chlorin e6 shows a proton signal near −1.8 ppm characteristically derived from the chlorin ring NH in $^1$H-NMR spectrum, while the proton signal has been disappeared for the gold complex. This has confirmed the formation of the gold complex.

Further, in view of the fact that the m/z value as actually measured at the mass spectrum analysis is 906 (M+H)$^+$ which is the same as the theoretical value, and that the values found in the elementary analysis are as given in the above, it was found that the gold complex of mono-L-aspartyl chlorin e6 as obtained in this Example had such molecular composition that the molecule of mono-L-aspartyl chlorin e6 had been deprived of three hydrogen atoms therefrom and one gold atom has been introduced thereinto. Accordingly, the gold complex of mono-L-aspartyl chlorin e6 which was obtained in the form of a dark green colored powdery substance in this Example is found to have the molecular formula (empirical formula): $C_{38}H_{38}AuN_5O_9$ and to be represented by the above-mentioned structural formula (Ia-1).

EXAMPLE 2

Preparation of a Sodium Salt of the Mono-L-aspartyl Chlorin e6-gold Complex

Mono-L-aspartyl chlorin e6-gold complex (100 mg) as obtained in Example 1 above was suspended in deionized water. To the resulting aqueous suspension was added 1N NaOH in an amount calculated, and the resultant mixture was stirred. After the completed dissolution, the resulting reaction solution was concentrated to dryness. Thus, a sodium salt of the mono-L-aspartyl chlorin e6-gold complex was obtained as a dark green colored amorphous powder (Yield: about 110 mg).

The gold complex sodium salt so obtained was analyzed for its infrared absorption spectrum and mass spectrum. The infrared absorption spectrum as measured is shown in FIG. 2 of the attached Drawings, and the mass spectrum as measured is shown in FIG. 4 of the attached Drawings.

Figure 4:
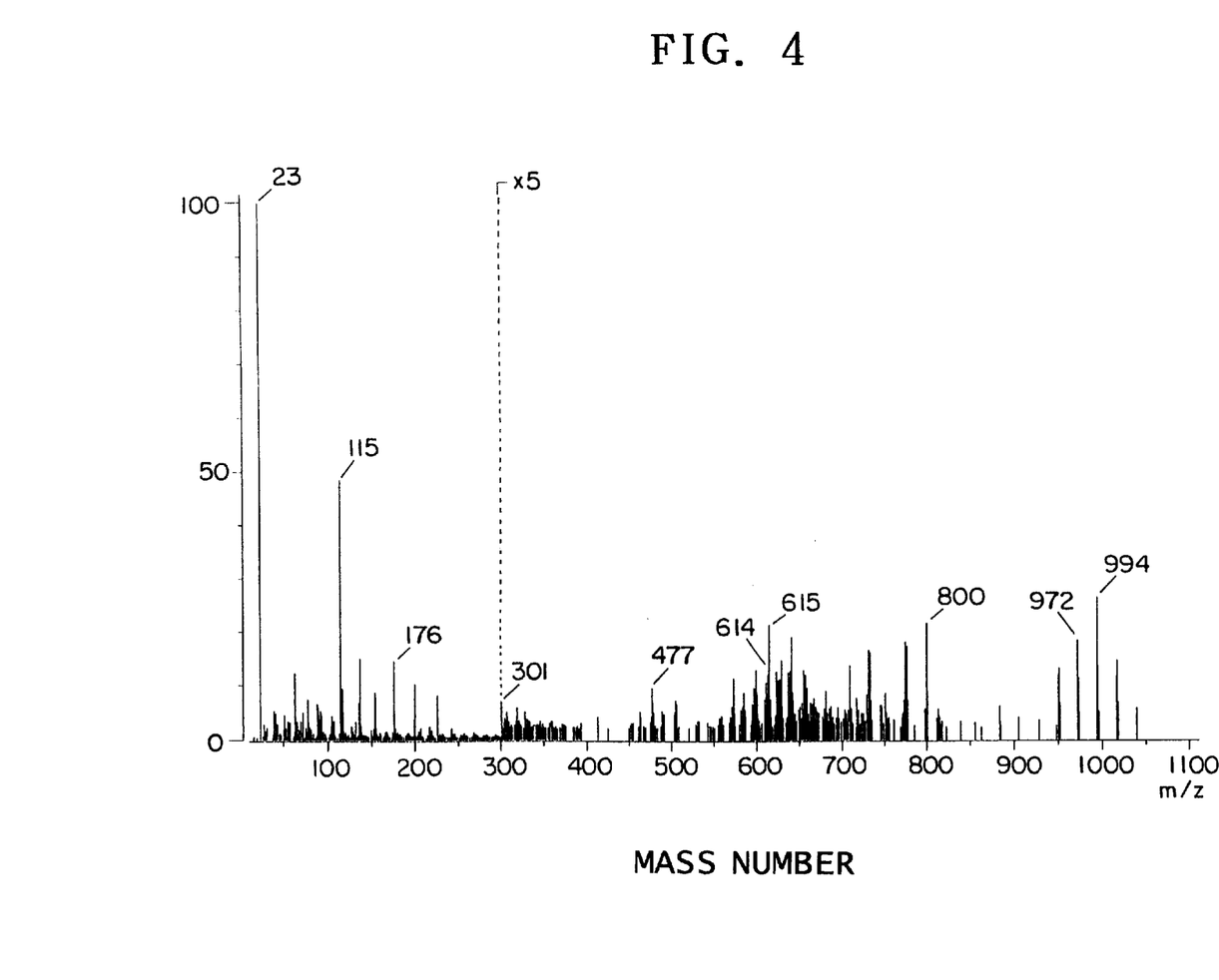
FIG. 4 shows a mass spectrum of mono-L-aspartyl chlorin e6-gold complex tetrasodium salt as prepared in Example 2 hereinafter given.

From the mass spectrum given in FIG. 4, the gold complex sodium salt as obtained in this Example has been found to have the m/z value of 972 in the mass spectrum analysis.

Figure 1:
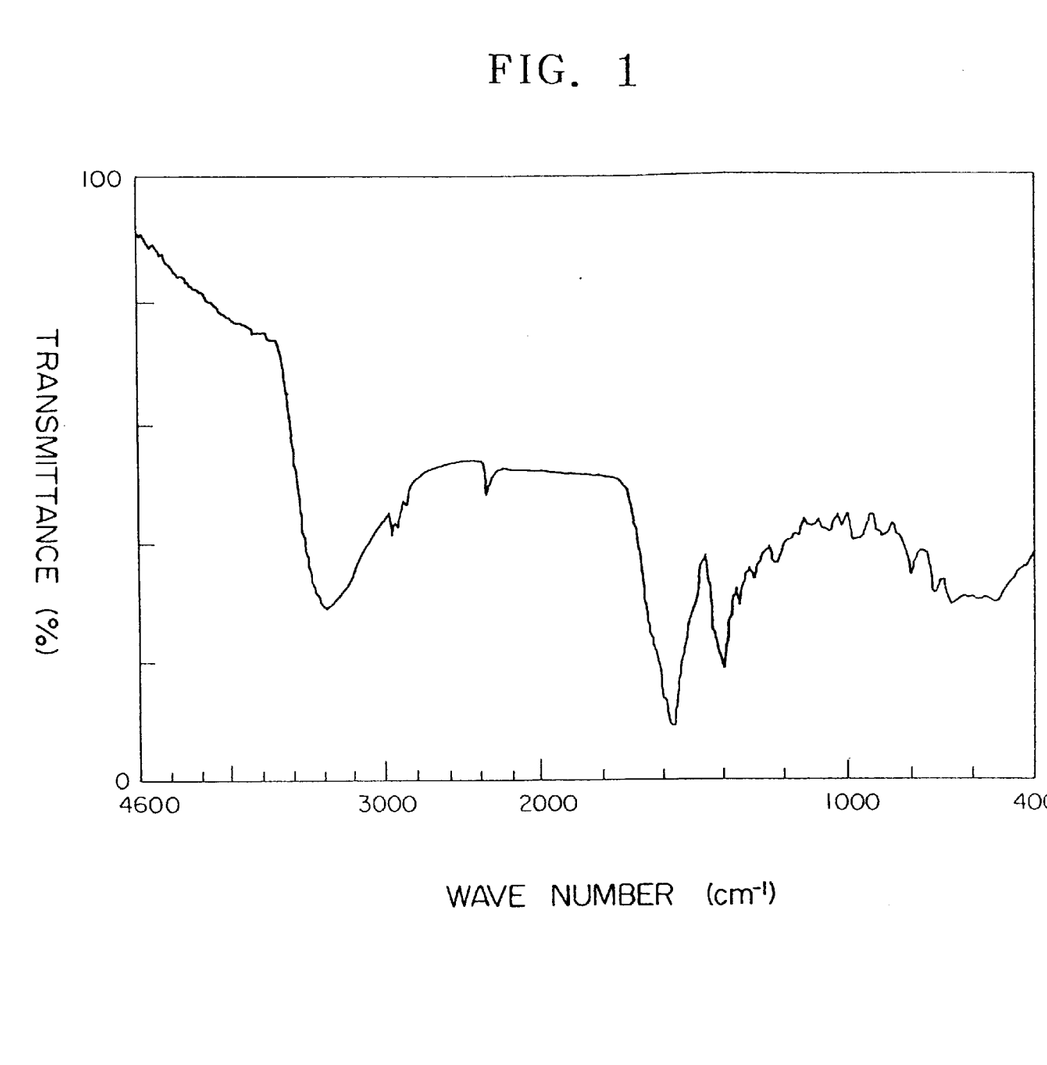
FIG. 1 shows an infrared absorption spectrum (measured by KBr method) of mono-L-aspartyl chlorin e6 tetrasodium salt.
Figure 2:
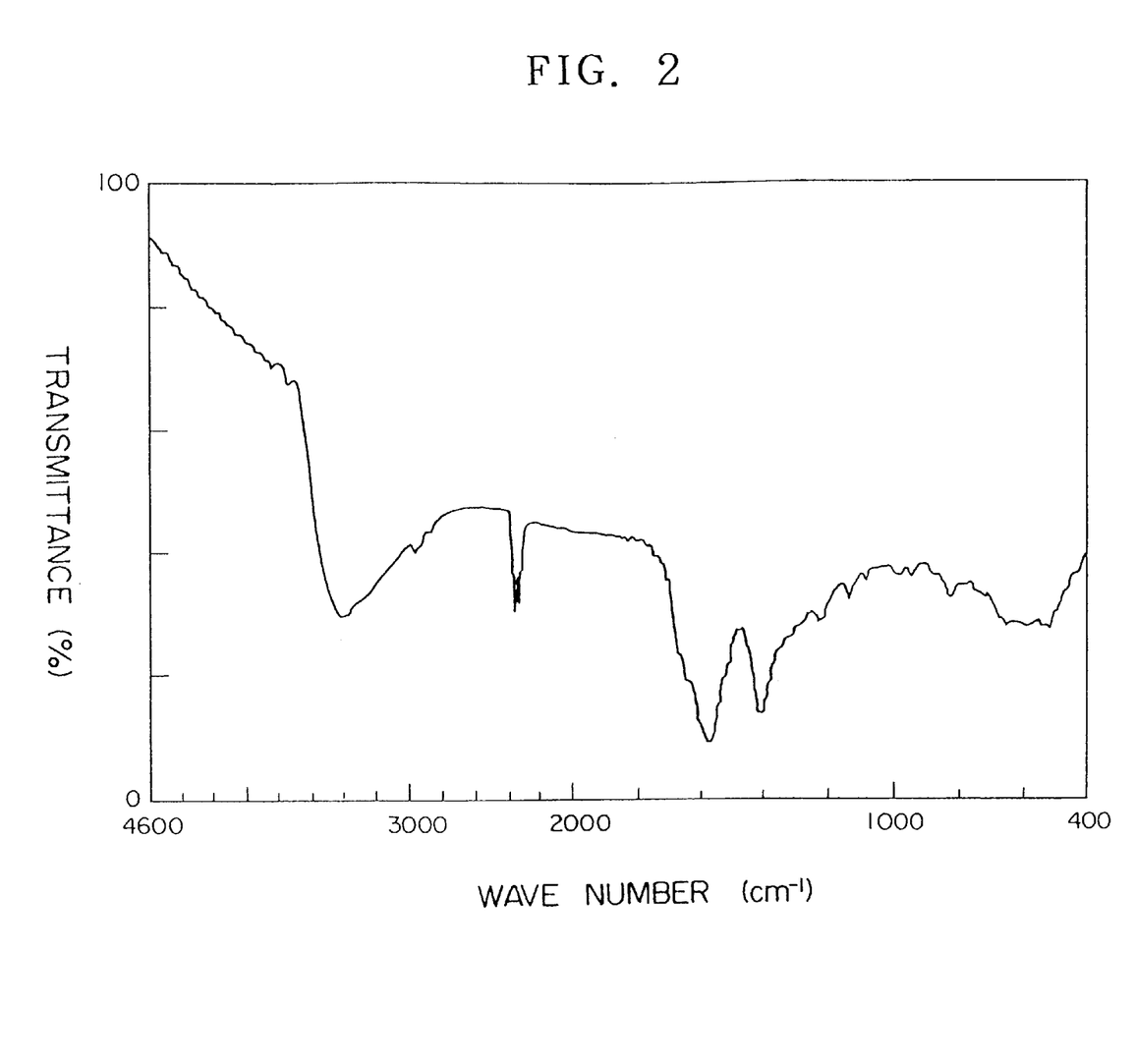
FIG. 2 shows an infrared absorption spectrum (measured by KBr method) of the mono-L-aspartyl chlorin e6-gold complex tetrasodium salt as prepared in Example 2 hereinafter given.

Further, from the comparison of FIG. 2 with FIG. 1 of the attached Drawings, it is shown that the pattern of infrared absorption spectrum of the mono-L-aspartyl chlorin e6-gold complex sodium salt shown in FIG. 2 is analogous to the pattern of infrared absorption spectrum of the mono-L-aspartyl chlorin e6 sodium salt shown in FIG. 1. Thus, it is confirmed that the structure of the chlorin skeleton has been maintained in the gold complex sodium salt which was obtained in Example 2 above.

TEST EXAMPLE 1

Detection and Therapy of Tumor Tissue by X-ray Radiography

Male Balb/c mice having a body weight of 16~20 g (five mice per group) were inoculated, in their abdominal region, with MKSA cells to form a solid ascites carcinoma in the abdominal region of mouse. The mono-L-aspartyl chlorin e6-gold complex sodium salt (the product of Example 2 above) was administered at a dose of 0.01~0.04 mg in the form of a physiological saline solution of said gold complex sodium salt to the cancer-bearing mice through their tail vein. At the end of one hour to three hours after the administration, the mice were anesthetized with nembutal. An X-ray beam containing the X-ray of the wavelength of 0.153 Å was irradiated from outside of the body to the abdominal region of the mice for an appropriate time.

X-ray image was formed by allowing the X-ray to pass through the abdominal region of mice and to expose and sensitize an X-ray film. Thus, an X-ray photograph in which the solid cancer to be detected had been sharply imaged was easily obtained, and thus the solid cancer could be easily detected from the resulting X-ray photograph with which the solid cancer tissue could be diagnosed.

One week after the X-ray irradiation, the mice was anatomized and inspected, when it could be observed that the dimensions of the solid cancer have been reduced significantly in comparison with those as observed at the time of taking the X-ray photograph. Thus, it was found and confirmed that the gold complex of the chlorin e6 derivative as administered to mice had exerted a cytocidal action to the ascites carcinoma cells upon the irradiation of X-ray to mice.

TEST EXAMPLE 2

Detection and Therapy of Lesions of Arteriosclerosis by X-ray Radiography

To a rabbit having a high cholesteremia and a body weight of about 4 kg was administered 8 mg of the mono-L-aspartyl chlorin e6-gold complex sodium salt (the product of Example 2) through the ear vein. One hour after the administration, anesthesia with nembutal was done to the rabbit. Then, the whole body of the rabbit was irradiated for an appropriate time with an X-ray beam containing the X-ray of the wavelength of 0.153 Å which suited to the electron absorption of the K-shell of gold atom. The X-ray which had passed through the rabbit was allowed to sensitize an X-ray film and to produce X-ray image. Thus, a sharp X-ray image of the lesions of arteriosclerosis of artery (the atheroselerotic layers of blood vessel) could be obtained, and therefore the lesions of arteriosclerosis could easily be detected.

One week after the X-ray irradiation, the rabbit was anatomized for necessary inspection, when the dimensions of the lesions of arteriosclerosis were found to have been clearly diminished in comparison with those as observed at the time of the X-ray irradiation thereto.

TEST EXAMPLE 3

The procedure of Test Example 1 was repeated except that the ascites carcinoma-bearing used in Test Example 1 were replaced by nude mice which had on the back of the body a solid cancer as formed by transplantation of PC-10 cells originated from human lung cancer. Sharp X-ray image of the solid cancer could be produced on X-ray film.

INDUSTRIAL APPLICABILITY

As explained in the above, this invention provides a novel X-ray-intercepting gold complex of the chlorin e6 derivative. The gold complex is able to specifically accumulate in the tissue of various tumors and in the lesions of arteriosclerosis within a mammal body and is able to afford a sharp X-ray image of the tumor and lesions of arteriosclerosis by irradiation of X-ray.

The novel X-ray-intercepting gold complex of the chlorin e6 derivative or a salt thereof is useful for conducting the detection, diagnosis and therapy of tumors, solid cancers or lesions of arteriosclerosis by X-ray radiography or X-ray irradiation. Also, an X-ray-intercepting platinum complex of the chlorin e6 derivative can be prepared.

What is claimed is:

1. An X-ray-intercepting gold complex of mono-L-aspartyl chlorin e6 or mono-L-glutamyl chlorin e6, which is produced by a coordinate bond or by chelation of a gold cation with the chlorin ring of mono-L-aspartyl chlorin e6 or mono-L-glutamyl chlorin e6, or a pharmacologically acceptable salt thereof.

2. An X-ray-intercepting gold complex of mono-L-aspartyl chlorin e6 or mono-L-glutamyl chlorin e6, with a mono, di or trivalent gold atom, which is represented by the following formula (I)

(I)

wherein Au stands for a gold atom, m stands for an integer of 1, 2 or 3 and n stands for an integer of 1 or 2, or pharmacologically acceptable salt thereof.

3. A gold complex as claimed in claim 2, where the gold complex is an X-ray-intercepting gold complex of mono-L-aspartyl chlorin e6 or mono-L-glutamyl chlorin e6 with a trivalent gold atom, which is represented by following formula (Ia)

(Ia)

wherein Au stands for a gold atom and n stands for an integer of 1 or 2, or pharmacologically acceptable salt thereof.

4. A gold complex as claimed in claim 3, where the gold complex represented by the formula (Ia) is an X-ray-intercepting gold complex of mono-L-aspartyl chlorin e6 with a trivalent gold atom which is represented by the following formula (Ia-1)

or a pharmacologically acceptable salt thereof.

5. A pharmacologically acceptable salt of the gold complex as claimed in claim 4, wherein the salt of the gold complex of the formula (Ia) is a sodium salt of the mono-L-aspartyl chlorin e6-gold complex of formula (Ia-1).

6. A pharmaceutical composition comprising, as an active ingredient, an X-ray-intercepting gold complex of mono-L-aspartyl chlorin e6 or mono-L-glutamyl chlorin e6 which is represented by formula (I)

wherein Au stands for a gold atom and n stands for an integer of 1 or 2, or pharmacologically acceptable salt thereof, in combination with a pharmaceutically acceptable solid or liquid carrier.

7. A method for the detection and diagnosis of tissue of tumor or solid cancer, which comprises administering to a mammal host having a tumor or solid cancer an X-ray-intercepting gold complex of the chlorin e6 derivative having the formula (I)

wherein Au stands for a gold atom, m stands for an integer of 1, 2 or 3 and n stands for an integer of 1 or 2, or an X-ray-intercepting gold complex of mono-L-aspartyl chlorin e6 or mono-L-glutamyl chlorin e6 which is represented by formula (Ia)

wherein Au stands for a gold atom, m stands for an integer of 1, 2 or 3 and n stands for an integer of 1 or 2, or a salt thereof, or an X-ray-intercepting gold complex of the chlorin e6 derivative having the formula (Ia)

wherein Au stands for a gold atom and n stands for an integer of 1 or 2, or a salt thereof, in an amount of the gold complex effective to permit the gold complex to accumulate in the tumor or solid cancer tissue, then irradiating from outside of the host body an X-ray beam containing X-ray of a wavelength of 0.153 Å towards the tumor or cancer, and taking a photograph of X-ray image of the tumor or solid cancer tissue having contained therein said gold complex, on an X-ray film by a technique of computed X-ray tomography, and making diagnosis of the tumor or cancer tissue.

8. A method for the detection and therapy of a tumor or solid cancer, which comprises administering to a mammal host having a tumor or solid cancer an X-ray-intercepting gold complex of the chlorin e6 derivative of the formula (I)

(I)

wherein Au stands for a gold atom, m stands for an integer of 1, 2 or 3 and n stands for an integer of 1 or 2, or a salt thereof, or an X-ray-intercepting gold complex of the chlorin e6 derivative of the formula (Ia)

wherein Au stands for a gold atom and n stands for an integer of 1 or 2, or a salt thereof, in an amount of the gold complex effective to permit the gold complex to accumulate in the tumor or solid cancer tissue, then irradiating from outside of the host body an X-ray beam containing X-ray of a wavelength of 0.153 Å towards the tumor or cancer, and taking a photograph of X-ray image of the tumor or solid cancer tissue having contained therein said gold complex, on an X-ray film by a technique of computed X-ray tomography, to detect the region of the tumor or solid cancer, and thereafter further irradiating to the region of the tumor or solid cancer an X-ray beam containing X-ray of the wavelength of 0.153 Å, so that cells of the tumor or solid cancer are killed by the actions of the gold complex as excited with the so irradiated X-ray and also by the electron as emitted from the gold atom of said complex.

9. A method for the detection and therapy of lesions of arteriosclerosis, which comprises administering to a mammal host having an arteriosclerosis a gold complex of the chlorin e6 derivative having the formula (I)

(I)

wherein Au stands for a gold atom, m stands for an integer of 1, 2 or 3 and n stands for an integer of 1 or 2, or a salt thereof, or a gold complex of the chlorin e6 derivative having the formula (Ia)

(Ia)

wherein Au stands for a gold atom and n stands for an integer of 1 or 2, or a salt thereof, in an amount of the gold complex effective to permit the gold complex to accumulate in the lesions of arteriosclerosis, then irradiating from outside of the host body an X-ray beam containing X-ray of a wavelength of 0.153 Å towards the arteriosclerosis lesions, and taking a photograph of X-ray image of the lesions of arteriosclerosis having contained therein said gold complex, on an X-ray film by a technique of computed X-ray tomography, to detect the region of the lesions of arteriosclerosis, and thereafter further irradiating to the region of the lesions of arteriosclerosis an X-ray beam containing X-ray of the wavelength of 0.153 Å, so that cholesterol-accumulated parts present within said lesions of arteriosclerosis are destroyed by the actions of the gold complex as excited with the so irradiated X-ray and also by the electron as emitted from the gold atom of said complex.

10. A process for the preparation of a purified product of the mono-L-aspartyl chlorin e6-gold complex of the formula (Ia-1)

which comprises the steps of reacting mono-L-aspartyl chlorin e6 tetra-sodium salt with 1~2 molar equivalents of hydrogen tetrachloroaurate ($HAuCl_4$) in a phosphate buffer solution having a 1/10~1/20 molar concentration (pH7.0~8.0) at a temperature of 0~50° C. until the reaction is completed, then adjusting the pH of the resulting reaction solution with addition of a dilute hydrochloric acid to pH 2.5~3.5, thereby depositing a precipitate comprising the gold complex of mono-L-aspartyl chlorin e6, collecting the precipitate, then dissolving the precipitate so collected in a phosphate buffer solution of 110~1120 molar concentration (pH 7.0~8.0) in order to achieve a purification of the gold complex, passing the resulting solution through a reversed phase column where a gel of octadecylsilica (ODS) is used as the immobile phase and water containing 5~15% (volume %) of methanol is used as the mobile phase, then collecting in fractions the effluent from the reversed phase column, concentrating the effluent fractions containing singly the mono-L-aspartyl chlorin e6-gold complex under a reduced pressure, adjusting the pH of the resultant concentrated solution with a dilute hydrochloric acid to pH 2.5~3.5, thereby depositing a precipitate of dark green color, collecting the precipitate, washing the resulting precipitate with water containing 40~50% (volume %) of acetone, separating the precipitate from the aqueous acetone by centrifugation, and drying further the precipitate made of said gold complex under a reduced pressure.

11. An X-ray-intercepting platinum complex of mono-L-aspartyl chlorin e6 or mono-L-glutamyl chlorin e6, which is prepared by a coordinate bond or by chelation of a platinum cation to the chlorin ring of mono-L-aspartyl chlorin e6 or mono-L-glutamyl chlorin e6, or a pharmacologically acceptable salt thereof.

12. An X-ray-intercepting platinum complex of mono-L-aspartyl chlorin e6 or mono-L-glutamyl chlorin e6, with a di or tetravalent platinum atom, which is represented by the following formula (II)

wherein Pt stands for a platinum atom, z stands for an integer of 2 or 4 and n stands for an integer of 1 or 2.

13. A platinum complex as claimed in claim 12, where the platinum complex of the chlorin e6 derivative having the formula (II) is an X-ray-intercepting platinum complex of mono-L-aspartyl chlorin e6 or mono-L-glutamyl chlorin e6 with a tetravalent platinum atom, which is represented by following formula (IIa)

wherein n stands for an integer of 1 or 2.

14. The method according to claim 7 wherein the x-ray intercepting gold complex of the chlorin e6 derivative comprises a mono-L-aspartyl chlorin e6-gold complex, which is represented by the following formula (Ia-1)

or a sodium salt thereof.

15. The method according to claim 8 wherein the x-ray intercepting gold complex of the chlorin e6 derivative comprises a mono-L-aspartyl chlorin e6-gold complex, which is represented by the following formula (Ia-1)

or a sodium salt thereof.

16. The method according to claim 9 wherein the x-ray intercepting gold complex of the chlorin e6 derivative comprises a mono-L-aspartyl chlorin e6-gold complex, which is represented by the following formula (Ia-1)

or a sodium salt thereof.

\* \* \* \* \*